United States Patent [19]
Field

[11] Patent Number: 4,560,820
[45] Date of Patent: Dec. 24, 1985

[54] ALKYLAROMATIC DEALKYLATION

[75] Inventor: Leslie A. Field, Oakland, Calif.

[73] Assignee: Chevron Research Company, San Francisco, Calif.

[21] Appl. No.: 664,658

[22] Filed: Oct. 25, 1984

Related U.S. Application Data

[63] Continuation of Ser. No. 253,976, Apr. 13, 1981, abandoned.

[51] Int. Cl.$^4$ ................................................ C07C 4/18
[52] U.S. Cl. ...................... 585/489; 585/486; 585/487; 585/488
[58] Field of Search ................ 585/486, 487, 488, 489

[56] References Cited

U.S. PATENT DOCUMENTS

| Re. 29,857 | 12/1978 | Argauer et al. ...................... 208/111 |
| 3,267,023 | 8/1966 | Miale et al. ...................... 585/486 X |
| 3,660,309 | 5/1972 | Hayes et al. ...................... 585/486 X |
| 3,716,596 | 2/1973 | Bowes ............................... 260/671 C |
| 3,829,519 | 8/1974 | Sampson et al. ................ 585/489 X |
| 3,856,873 | 12/1974 | Burress ............................ 585/486 X |
| 3,926,782 | 12/1975 | Plank et al. ...................... 585/486 X |
| 3,945,913 | 3/1976 | Brennan et al. ...................... 208/137 |
| 4,066,531 | 1/1978 | Owen et al. ........................... 208/120 |
| 4,247,730 | 1/1981 | Brunelle ........................... 585/486 X |
| 4,320,242 | 3/1982 | Onodera et al. ...................... 585/489 |
| 4,469,909 | 9/1984 | Chester et al. .................. 585/489 X |

FOREIGN PATENT DOCUMENTS

| 0027157 | 4/1981 | European Pat. Off. . |
| 937260 | 9/1963 | United Kingdom ................ 585/486 |
| 1240115 | 7/1971 | United Kingdom ................ 585/489 |

Primary Examiner—Thomas A. Waltz
Attorney, Agent, or Firm—S. R. LaPaglia; W. K. Turner; V. J. Cavalieri

[57] ABSTRACT

A process for dealkylating alkylaromatic hydrocarbons using intermediate pore size zeolites substantially free of acidity is disclosed.

13 Claims, No Drawings

ALKYLAROMATIC DEALKYLATION

This is a continuation of application Ser. No. 253,976, filed Apr. 13, 1981, now abandoned.

TECHNICAL FIELD

Benzene is one of the basic raw materials of the chemical industry. It is used to synthesize rubbers, dyes, and detergents and is also used as a solvent and as an octane increasing gasoline additive. Benzene is usually produced from hydrocarbonaceous feed materials in a mixture with toluene, the xylenes, and higher aromatics through reforming reactions such as cyclization, dehydrogenation, and isomerization. Benzene is also produced during the dealkylation of $C_7+$ aromatics and during disproportionation reactions of toluene and the xylenes over zeolites. The benzene produced by disproportionation reactions, of toluene for example, also contains higher ($C_8+$) alkylaromatics such as the xylenes.

Recovery of purified benzene from the mixtures prepared by disproportionation requires some further treatment, for example, some combination of fractionation, solvent extraction, and adsorptive extraction. The efficiency of these separation steps increases as the benzene content of the reformate increases. Standard dealkylation reactions can produce good quality benzene, but require severe reaction conditions. There has been no particularly efficient process for producing a high-benzene containing dealkylate or for producing a high-benzene disproportionate which need not be fractionally distilled, solvent extracted, or further dealkylated to obtain a high benzene content feed suitable for subsequent purification steps.

The object of the present invention is to provide such a process.

I have discovered that intermediate pore size zeolites can be used to dealkylate $C_7+$ alkylaromatics, and especially toluene. Most surprisingly, the primary constituent of the product is benzene, even when toluene is the feed and disproportionation would be expected. Benzene production using my process becomes much more efficient than processes known to the art. Additionally, the reaction conditions for my dealkylation process are mild when compared to the severe conditions of standard dealkylation techniques known to the art. The importance of this development can scarcely be overestimated in view of the increasing demands for benzene by the chemical and the automotive industries, and in view of the decreasing amounts of petroleum feeds available to the world market.

BACKGROUND ART

A number of U.S. patents relate to the production of benzene/toluene/xylene (BTX) mixtures from various feeds, and the disproportionation of toluene or xylene to benzene and other aromatics.

U.S. Pat. No. 3,716,596, Bowes, Feb. 13, 1973, discloses alkylaromatic dealkylation using ZSM-4.

U.S. Pat. No. RE 29,857 of U.S. Pat. No. 3,790,471, Argauer, Feb. 5, 1974, discloses toluene disproportionation using ZSM-5.

U.S. Pat. No. 3,945,913, Brennan, Mar. 23, 1976, discloses the preparation of BTX from alkylaromatics having nine or more carbon atoms using ZSM-5.

U.S. Pat. No. 4,066,531, Owen, Jan. 3, 1978, discloses using ZSM-5 to process a heavy reformate feedstock ($C_8+$ alkylaromatics) from which benzene has been removed to produce BTX.

The preceding patents relate to disproportionation reactions. The well-known dealkylation reactions of the art, typically operate at very severe conditions. The usual feed, toluene, is typically heated to 590° C. to 650° C. at pressures of from 25–40 bar for both thermal and catalytic processes; thermal dealkylation is performed at temperatures up to 760° C.

TECHNICAL DISCLOSURE

My invention is embodied in a process for preparing a product having a substantial benzene content from $C_7$ and higher alkylaromatics, comprising:

(a) contacting a hydrocarbonaceous feed, which comprises $C_7$ and higher alkylaromatics, with a conversion catalyst which comprises an intermediate pore size zeolite and a platinum compound, and wherein said zeolite is substantially free of acidity; and (b) recovering a benzene containing effluent.

Feeds appropriate for use in the process contain toluene, m-xylene, p-xylene, ethylbenzene and dealkylatable $C_9+$ alkylaromatics such as isopropylbenzene. Typical hydrocarbonaceous feedstocks appropriate for use have a boiling range of above about 40° C. and below about 300° C., preferably above about 60° C. and below about 150° C. Normal feeds for refinery production of benzene and for dealkylation include reformates produced from light straight-run fractions and light naphthas. Whatever the feed source, the higher the proportion of $C_7$ and higher dealkylatable alkylaromatics in the feed, especially toluene and meta- and para-xylene, the greater the efficiency of the process, and the higher the benzene content of the effluent. The most preferred feeds consist essentially of single ring aromatic hydrocarbons having from 7 to 9 carbon atoms, most especially, toluene. By "dealkylatable" as used herein is meant alkylaromatic compounds which have kinetic diameters which allow them to fit within the intermediate pore size zeolites; and, alkylaromatic compounds whose kinetic diameters are too large to fit within the zeolites but which isomerize or crack in situ during processing to form other alkylaromatics having kinetic diameters which do allow them to diffuse into the zeolites.

The intermediate pore size zeolites used in the process are crystalline aluminosilicate zeolites having a silica to alumina mol ratio greater than about 10:1 and preferably greater than about 40:1. These zeolites have useful activity even at high silica:alumina mol ratios such as 1000 to 2000:1.

By "intermediate pore size" as used herein is meant an effective pore aperture in the range of about 5 to 6.5 Angstroms when the zeolite is in the H-form. Zeolites having pore apertures in this range tend to have unique molecular sieving characteristics. Unlike small pore zeolites such as erionite, they will allow hydrocarbons having some branching into the zeolite void spaces. Unlike large pore zeolites such as the faujasites, they can differentiate between n-alkanes and slightly branched alkanes on the one hand and larger branched alkanes having, for example, quaternary carbon atoms.

The effective pore size of the zeolites can be measured using standard adsorption techniques and hydrocarbonaceous compounds of known minimum kinetic diameters. See Breck, *Zeolite Molecular Sieves*, 1974 (especially Chapter 8) and Anderson et al., J. Catalysis 58, 114 (1979), both of which are incorporated by reference.

Intermediate pore size zeolites in the H-form will typically admit molecules having kinetic diameters of 5 to 6 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular zeolite, but do not penetrate as quickly and in some cases, are effectively excluded (for example, 2,2-dimethylbutane is excluded from H-ZSM-5). Compounds having kinetic diameters in the range of 6 to 6.5 Angstroms include: cyclohexane (6.0), 2,3-dimethylbutane (6.1), 2,2-dimethylbutane (6.2), m-xylene (6.1) and 1,2,3,4-tetramethylbenzene (6.4). Generally, compounds having kinetic diameters of greater than about 6.5 Angstroms cannot penetrate the pore apertures and thus cannot be adsorbed in the interior of the zeolite. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. ZSM-5, ZSM-11, and silicalite, for example, fall within this range.

In performing adsorption measurements to determine pore size, standard techniques are used. It is convenient to consider a particular molecule as excluded if it does not reach at least 95% of its equilibrium adsorption value on the zeolite in less than about 10 minutes (P/Po=0.5, 25° C.).

Examples of intermediate pore size zeolites include, CZH-5, silicalite and members of the ZSM series such as ZSM-5, ZSM-11, ZSM-12, ZSM-21, ZSM-23, ZSM-35, and ZSM-38.

CZH-5 is described in Ser. No. 166,863, Hickson, filed July 7, 1980, incorporated herein by reference. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 is described in U.S. Pat. No. 3,948,758; and silicalite is described in U.S. Pat. No. 4,061,724. These patents are incorporated herein by reference. The preferred zeolites are silicalite, ZSM-5, and ZSM-11.

The conversion catalyst must include a platinum compound. The metal component can be impregnated into the zeolite after it is formed, or the metal can be included in the reaction mixture from which the zeolite is hydrothermally crystallized. It is highly desirable for the metal component to be dispersed uniformly throughout the zeolite. For this reason, it is highly preferred to prepare the zeolite from a hydrothermal crystallization mixture, which contains a platinum component, thereby occluding the platinum component within the zeolite pores. The amount of metal present in the conversion catalyst should be within the normal range of use in reforming catalysts, from about 0.1 to 1.0 weight percent, preferably 0.2 to 0.8 weight percent, and most preferably 0.2 to 0.6 weight percent. It appears that the catalytic activity allowing the dealkylation comes from both the platinum component and the zeolite component.

Reforming catalysts containing platinum are usually subjected to halogen or halide treatments to achieve or maintain a uniform metal dispersion and they also contain a halide component (especially a chlorine compound). The catalysts of my invention can be subjected to similar treatments without lessening the catalytic specificity for benzene containing dealkylate. The halide treatment does not appear to have a significant effect on the yield of benzene.

The intermediate pore size zeolite/platinum conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

The conversion catalyst must be substantially free of acidity, for example, by poisoning the zeolite with a basic metal, e.g., alkali metal, compound. Intermediate pore size zeolites are usually prepared from mixtures containing alkali metal hydroxides and thus have alkali metal contents of about 1 to 2 weight percent. These high levels of alkali metal, usually sodium or potassium, are unacceptable for most catalytic applications because they cause a high fouling rate. Usually, the alkali metal is removed to low levels by ion-exchange with hydrogen or ammonium ions. By "alkali metal compound" as used herein is meant elemental or ionic alkali metals or their basic compounds. Surprisingly, unless the zeolite itself is substantially free of acidity, a basic compound is required in the present process to direct the synthetic reactions to benzene production.

The amount of alkali metal necessary to render the zeolite substantially free of acidity can be calculated using standard techniques based on the aluminum content of the zeolite. Under normal circumstances, the zeolite as prepared and without ion-exchange will contain sufficient alkali metal to neutralize the acidity of the catalyst. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

The preferred basic metals are sodium and potassium.

The zeolite itself can be substantially free of acidity only at very high silica:alumina mol ratios; by "zeolite consisting essentially of silica" is meant a zeolite which is substantially free of acidity without base poisoning. By "substantially free of acidity" for these sorts of zeolites is meant a component without activity as determined in standard catalytic cracking tests.

The reaction conditions for the process typically include pressures ranging from atmospheric to 10 bar, and liquid hourly space velocities (LHSV) ranging from 0.1 to 15. Hydrogen beyond that necessary for the stoichiometry of the reaction can be mixed with the feed to lessen the tendency of the catalyst to foul. The reactions can take place at temperatures above 450° C. and can be conducted at temperatures ranging up to 595° C. Surprisingly, the dealkylation process is most efficient at relatively low temperatures, above 475° C. and ranging up to about 550° C.

By "substantial amount of benzene" is meant a benzene content of the $C_5^+$ aromatics produced which is greater than about 50% by weight of the $C_5^+$ aromatics, preferably greater than about 60% by weight, and most preferably greater than about 75% by weight.

The following examples illustrate the invention. All percentages given are by weight, unless otherwise indicated.

EXAMPLE 1

Experiments were performed to show the effect of not having platinum on the catalyst; disproportionation of toluene to benzene and the xylenes took place rather than dealkylation to benzene. The feed used was toluene and reaction conditions included LHSV=1, 3.3 bar (gauge), $H_2/HC=1$, and 538° C. The toluene feed contained about 1.2% $C_8+$. The zeolites were prepared according to U.S. Pat. No. 4,061,724. The zeolites were not composited with an inorganic matrix.

|  | A | B |
|---|---|---|
| Catalyst |  |  |
| $SiO_2:Al_2O_3$ | 892 | 892 |
| Na, % | 4.12 | 4.12 |
| Pt, % | 0 | 0 |
| Product |  |  |
| Toluene, % in aromatics | 98.61 | 99.65 |
| Benzene, % of non-toluene aromatics | 10.90 | 37.16 |
| $C_8+$, % in non-toluene aromatics | 89.10 | 62.84 |

These data show that in the absence of platinum, the conversion of toluene is low, and the conversion which does occur, takes place by disproportionation to produce approximately equal amounts of toluene and xylenes.

EXAMPLE 2

Experiments were performed to contrast with those of the preceding example and to show the effect of the presence of platinum in the intermediate pore size zeolite catalyst. The zeolite was prepared according to U.S. Pat. No. 4,061,724 and was not composited with an inorganic matrix. The reaction conditions included 538° C., LHSV=1, $H_2/HC=1$, and 3.3 bar (gauge). The toluene feed was contaminated with 1.2% $C_8$ aromatics.

|  | C | D | E |
|---|---|---|---|
| Catalyst |  |  |  |
| $SiO_2:Al_2O_3$ | 892 | 892 | 892 |
| Na, % | 4.12 | 4.12 | 4.12 |
| Pt, % | 0.45 | 0.45 | 0.45 |
| Products |  |  |  |
| Toluene, % in aromatics | 81.26 | 88.05 | 88.39 |
| Benzene, % in non-toluene aromatics | 91.45 | 86.94 | 85.52 |
| $C_8+$, % in non-toluene aromatics | 8.55 | 13.06 | 14.49 |
| $C_8+$, % in aromatics | 1.6 | 1.6 | 1.7 |

These data show the selective production of benzene from toluene by dealkylation without significant coproduction of xylenes by disproportionation. The xylenes for the product are primarily those present in the feed. A product high in benzene content can easily be produced in significant quantities by removing the benzene from the product and recycling the remainder of the unreacted toluene product to extinction.

Another set of experiments was performed using the same catalyst and reaction conditions except at a temperature of 482° C.

| Product | F | G |
|---|---|---|
| Toluene, % in aromatics | 77.2 | 82.77 |
| Benzene, % in non-toluene aromatics | 96.20 | 92.48 |
| $C_8+$, % in non-toluene aromatics | 3.80 | 7.52 |
| $C_8+$, % in aromatics | 1.1 | 1.3 |

EXAMPLE 3

Experiments were performed to compare the process of the present invention to the reaction of toluene over a low sodium, zinc containing catalyst exhibiting the x-ray diffraction pattern of ZSM-5. The catalyst contained 0.94% zinc, 0.016% sodium, and was composited in an alumina matrix. The toluene feed contained 1.2% $C_8$ alkylaromatics; the reaction conditions included 3.3 bar (gauge), LHSV=1, $H_2/HC=1$, and 538° C.

| Product | H | I |
|---|---|---|
| Toluene, % in aromatics | 58.96 | 59.98 |
| Benzene, % in non-toluene aromatics | 42.91 | 43.26 |
| $C_8+$, % in non-toluene aromatics | 57.09 | 56.74 |
| $C_8+$, % in aromatics | 23.4 | 22.7 |

These experiments illustrate the disproportionation mechanism typical of the art ZSM-5 processes. Toluene produces approximately equal amounts of benzene and xylenes, while in the present dealkylation process, primarily benzene is produced.

I claim:

1. A process for preparing a product having a substantial benzene content from $C_7$ and higher alkylaromatics, comprising:
   (a) contacting a hydrocarbonaceous feed, which comprises dealkylatable $C_7$ and higher alkylaromatics at a temperature of from about 450° C. to 595° C., with a conversion catalyst, which comprises an intermediate pore size zeolite and platinum or a compound thereof and wherein said zeolite is substantially free of acidity, and has a silica:alumina mole ratio greater than about 10:1, under dealkylation conditions; and
   (b) recovering a benzene-containing effluent wherein the benzene content of the $C_5+$ aromatics produced is greater than about 75% by weight.

2. A process according to claim 1 wherein the intermediate pore size zeolite has pore apertures in the range of about 5 Angstroms to about 6.5 Angstroms.

3. A process according to claim 1 wherein said zeolite is selected from ZSM-5, ZSM-11, and silicalite.

4. A process according to claim 1 wherein said zeolite has an alkali metal content of about 100%, or greater, of the acid sites in said zeolite on a molar basis.

5. A process according to claim 4 wherein said alkali metal is selected from potassium and sodium.

6. A process according to claim 1 wherein said zeolite consists essentially of silica.

7. A process according to claim 1 wherein said feed has a boiling range above about 60° C. and below about 150° C.

8. A process according to claim 7 wherein said feed consists essentially of alkylaromatic hydrocarbons having from 7 to 9 carbon atoms.

9. A process according to claim 8 wherein said feed consists essentially of toluene.

10. A process according to claim 1 wherein said contacting occurs at a temperature above about 450° C.

11. A process according to claim 1 wherein said contacting occurs at a temperature above about 475° C.

12. A process according to claim 1 wherein said conversion catalyst further comprises a halide component.

13. The process of claim 1 further comprising the step of recycling unreacted alkylaromatics into said feed.

* * * * *